United States Patent
Boamfa et al.

(10) Patent No.: US 8,502,166 B2
(45) Date of Patent: Aug. 6, 2013

(54) MOLECULAR DIAGNOSTIC SYSTEM BASED ON EVANESCENT ILLUMINATION AND FLUORESCENCE

(75) Inventors: Marius Iosif Boamfa, Eindhoven (NL); Maarten Marinus Johannes Wilhelmus Van Herpen, Eindhoven (NL); Derk Jan Wilfred Klunder, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 313 days.

(21) Appl. No.: 12/864,910

(22) PCT Filed: Jan. 26, 2009

(86) PCT No.: PCT/IB2009/050300
§ 371 (c)(1),
(2), (4) Date: Jul. 28, 2010

(87) PCT Pub. No.: WO2009/098605
PCT Pub. Date: Aug. 13, 2009

(65) Prior Publication Data
US 2010/0320397 A1 Dec. 23, 2010

(30) Foreign Application Priority Data
Feb. 4, 2008 (EP) .................................. 08151036

(51) Int. Cl.
*G01N 21/64* (2006.01)
(52) U.S. Cl.
USPC ........................................................ 250/458.1
(58) Field of Classification Search
USPC .................................................. 250/458.1
See application file for complete search history.

(56) References Cited

U.S. PATENT DOCUMENTS

| 5,168,157 A | * | 12/1992 | Kimura .......................... 250/234 |
| 5,192,510 A | | 3/1993 | Zoha et al. |
| 5,583,342 A | * | 12/1996 | Ichie .......................... 250/459.1 |
| 5,633,724 A | | 5/1997 | King et al. |
| 5,639,668 A | | 6/1997 | Neel et al. |
| 5,939,709 A | | 8/1999 | Ghislain et al. |
| 6,340,598 B1 | | 1/2002 | Herron et al. |

(Continued)

FOREIGN PATENT DOCUMENTS

| CN | 1434287 A | 8/2003 |
| DE | 19747572 C1 | 4/1999 |

(Continued)

OTHER PUBLICATIONS

Johnson-White et al: "Reduction of Background Signal in Automated Array Biosensors"; Measurement Science and Technology, vol. 16, 2005, N29-N31.

(Continued)

*Primary Examiner* — Marcus Taningco

(57) ABSTRACT

An illumination detection system includes an excitation radiation source and associated radiation processing arrangement for focusing the excitation radiation from the radiation processing arrangement onto an analysis region of a sample. A radiation collection arrangement collects radiation from the analysis region of the sample resulting from the excitation, and a detector detects the collected radiation. The focused excitation radiation includes an excitation line which is evanescent in the sample. This combines the advantages of line scanning (reduced analysis time) and evanescent excitation (reduced background signal) and therewith enables increase measurement speed and precision for point of care application.

12 Claims, 3 Drawing Sheets

U.S. PATENT DOCUMENTS

| | | |
|---|---|---|
| 7,175,811 B2 | 2/2007 | Bach et al. |
| 2004/0021867 A1 | 2/2004 | Karthe et al. |
| 2006/0257886 A1* | 11/2006 | Kobayashi et al. ............... 435/6 |
| 2007/0206187 A1* | 9/2007 | Lundquist et al. ............ 356/318 |

FOREIGN PATENT DOCUMENTS

| | | | |
|---|---|---|---|
| DE | 19923563 | A1 | 12/2000 |
| EP | 0575132 | A1 | 12/1993 |
| JP | 2003344273 | A | 12/2003 |
| WO | 8704247 | A1 | 7/1987 |
| WO | 9306241 | A1 | 4/1993 |
| WO | 2004113886 | A1 | 12/2004 |

OTHER PUBLICATIONS

Wang et al:"Improving the Sensitivity of Protein Microarray by Evanescent-Field-Induced Fluorescence"; Journal of Zhejiang University Science, 2005, vol. 6A, No. 7, pp. 623-626.

Burghardt et al: "In Situ Fluorescent Protein Imaging With Metal Film-Enhanced Total Internal Reflection Microscopy"; Biophysical Journal, vol. 90, Jun. 2006, pp. 4662-4671.

* cited by examiner

MOLECULAR DIAGNOSTIC SYSTEM BASED ON EVANESCENT ILLUMINATION AND FLUORESCENCE

FIELD OF THE INVENTION

The invention relates to illumination detection systems and methods, particularly in the field of molecular diagnostics.

BACKGROUND OF THE INVENTION

One example of illumination used in detection systems is fluorescence, and an example of the use of fluorescence detection is in nucleic acid testing (NAT). This is a core element in molecular diagnostics for detecting genetic predispositions for diseases, for determining RNA expression levels or identification of pathogens, like bacteria and viruses that cause infections.

The detection of fluorescence can be used both for a qualitative determination of the presence of a particular target DNA sample, and for a quantitative determination of the amount of DNA present in a sample. This invention relates to the apparatus used to detect the fluorescence, and the method of use.

In a typical molecular diagnostic experiment, a bio-sample is screened for detection of certain biological components (the "target"), such as genes or proteins. This is done by detecting the occurrence of selective bindings (known as hybridization) of the target to a capture probe, which is attached to a solid surface. The hybridization step is typically followed by a washing step, where all unbounded target molecules are flushed away, and finally a detection step is carried out.

The detection is based on fluorescent detection of fluorescent labels attached to the target molecules. The fluorescent detection needs to be very sensitive, and surface specific so as to minimize the biological background. Ideally, the fluorescent detection needs to be capable of single fluorescent label detection, while the process is kept time effective.

In the near future, the detection needs to be performed outside the hospitals or laboratories set up for diagnostics. This requires that the devices are capable of sensitive measurement in relatively short time.

One of the limitations of fluorescence detection in biosensors is this biological background signal. In a typical experiment, fluorescence of molecules bound to a surface needs to be detected. However, the bio-components in the vicinity of the surface can generate a large background signal. Hence relatively long measurement times are needed to compensate with the background. A standard method to mitigate this problem is to use confocal filtering, so that the excitation from a small volume is imaged onto the detector used.

However, a problem with the use of a confocal optical system is again the length of the detection process, as the spot focus needs to be scanned across the area of interest of the sample in order to ensure reliability and sensitivity.

One proposed solution to this problem is to implement line scanning fluorescence detection. A focused line is scanned across the sample, so that the detection time can be reduced. However, the confocal filtering is not optimal in the direction along the axis of the line of excitation. This has the direct result that the detected surface fluorescence is affected by a relatively large background signal and the sensitivity is reduced.

SUMMARY OF THE INVENTION

It is an object of the invention to provide an analysis system and method for use in point of care diagnostics. in which a high measurement speed can be implemented but without significant loss of sensitivity and/or surface specificity.

The invention is defined by the independent claims. The dependent claims define advantageous embodiments.

According to the invention, there is provided an illumination detection system.

With a system according to the invention the strength of increased speed line scanning detection is enabled without suffering from loss of sensitivity. The use of a line focus for increased scanning speed, causes confocality in the line direction to be reduced. Hence, sensitivity of this type of detection is reduced. To compensate for this effect, evanescent excitation is incorporated. Making use of evanescent excitation gives an enhanced surface specificity, so that a sensitivity enhancement in detection is achieved. The invention thus combines the advantages of line scanning (reduced analysis time) and evanescent excitation (reduced background signal). This enables point of care diagnostic applications as outlined here above.

The associated radiation processing arrangement preferably comprises a beam shaping transformer for generating an annular beam shape. This annular beam shape can be used to generate evanescent excitation of the sample with the excitation radiation. In particular, when the beam is focused, if the light has an angle of incidence to the sample which exceeds the critical angle, there will be total internal reflection in the sample, and only near field evanescent light will enter the sample, to excite the sample. The beam shaping element can for example generate an annular beam shape from a plane parallel circular cross section wave front at the output of the excitation radiation source. The cross section need however not be circular and may be for example oval, rectangular or even square. In fact any shape will do as long as the critical angle requirement is fulfilled to obtain the evanescent excitation as further elucidated herein below.

The associated radiation processing arrangement preferably also comprises a line forming element for generating a beam shape from the annular beam which is mapped by the focusing arrangement to an excitation line. This provides the line illumination, to enable scanning in only one direction to implement a scan over a 2D sample area. The line forming element can for example comprise a cylindrical lens or phase plate.

The radiation collection arrangement is preferably for collecting luminescence radiation, i.e. fluorescence radiation and/or phosphorescence radiation from the sample. Preferably fluorescence radiation detection is used as this is most sensitive and is based on an instantaneous process.

The system can be used to analyze any sample that can be excited. Such samples include materials of all kinds being solid, liquid or gaseous if they are attached to the surface. Preferably, the sample comprises analysis surfaces in the form of sites or chambers which may carry or contain chemicals to be analyzed. Such chambers may be reaction vessels of all volumes. Preferably, the system comprises an oligo- or polynucleotide, such as for example DNA or RNA, analysis system. Such systems include those based on replication of such materials and include for example polymerase chain reaction replication or other replication techniques.

The focusing arrangement and the radiation collection arrangement can share an excitation/collection lens. This simplifies the system which is desired in view of stability and use in the field outside the hospital. Manufacturing cost will also be reduced According to the invention there is also provided a method of measuring an analysis radiation from a sample using an illumination detection system. The method provides inter alia the advantages as explained here above in relation to the apparatus.

BRIEF DESCRIPTION OF THE DRAWINGS

Examples of the invention will now be described in detail with reference to the accompanying drawings, in which.

DETAILED DESCRIPTION OF EMBODIMENTS

The invention relates to a radiation analysis apparatus and method which combines line scanning detection with evanescent excitation. Making use of evanescent excitation gives an enhanced surface specificity, so that a sensitivity enhancement in fluorescence detection is achieved, and this enables a higher speed line scanning approach to be adopted.

Figure 1:
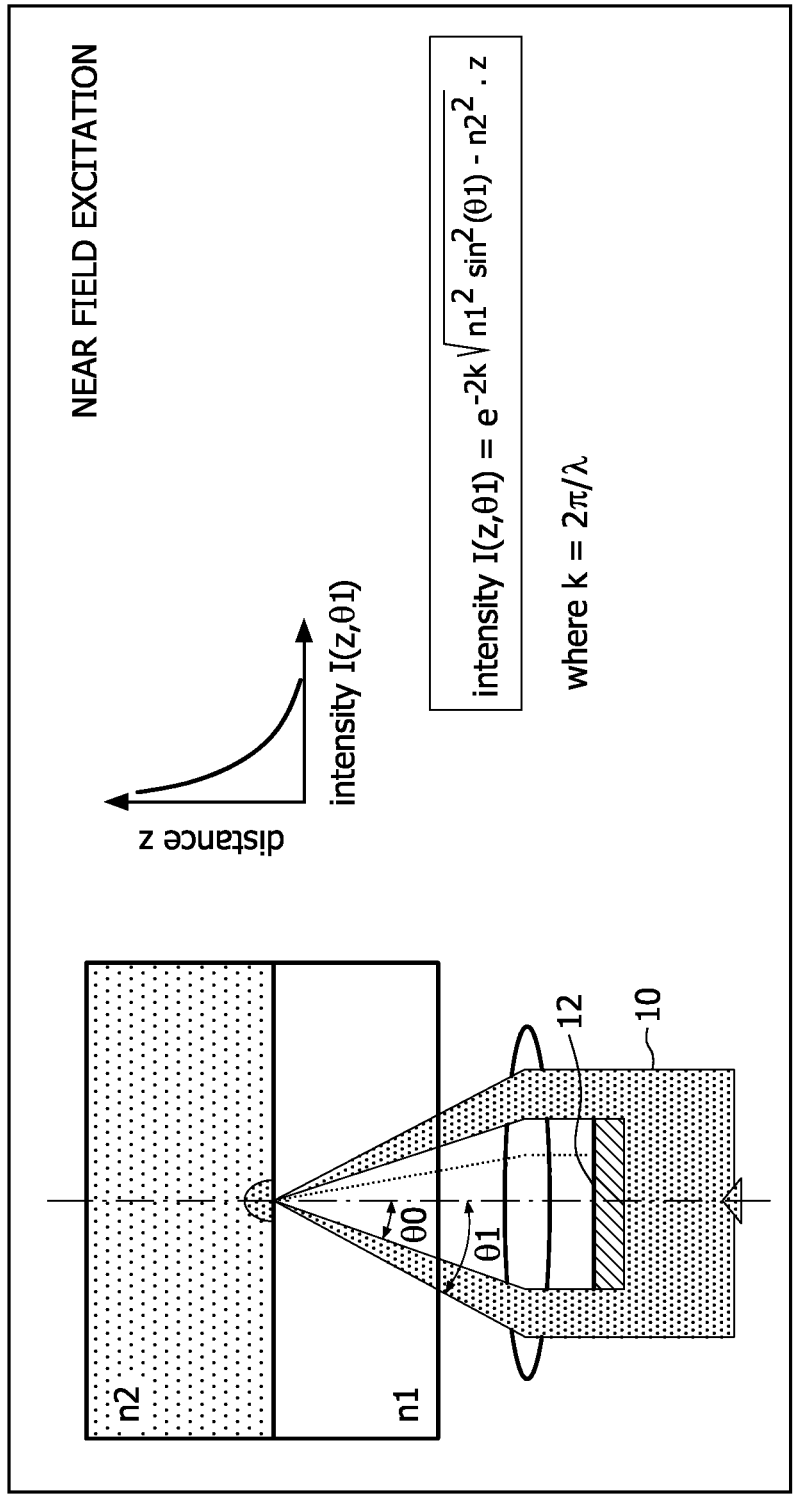
FIG. 1 is used to illustrate the principle of evanescent excitation.

The principle of evanescent excitation will first be explained with reference to FIG. 1. In this example the radiation is optical radiation or light. The detected radiation is fluorescence radiation. Those skilled in the art will know that other types of radiation such as UV radiation may also be used.

A radiation excitation source in the form of a laser is used to provide laser beam 10 which is focused from a high refractive index medium n1 (e.g. glass) into a low refractive index medium n2 (e.g. water). For angles smaller than the critical angle θ0, the light will be transmitted into medium n2. However, a beam shaping arrangement 12 can be used block the central part of the incoming beam such that no light is transmitted into medium n2. This removes the bulk excitation of the medium n2. For angles greater than the critical angle θ0, total internal reflection occurs at the interface between the two media and an evanescent wave may travel into the low refractive index medium n2, with a decaying field amplitude I(Z, θ1) as a function of propagation distance (z). Since this evanescent wave is rapidly decaying in the z direction, it can be used to probe only those entities or molecules that are present near the surface of the interface between the layers with n1 and n2.

Upon excitation with a (short wavelength) laser, the fluorescent molecules will start radiating light in all directions. The wavelength of the fluorescent light will be longer than the excitation wavelength.

The beam shaping arrangement in this example configuration can be a central dichroic mask, which is arranged to be transparent for the fluorescence wavelengths, thereby maximizing the collection efficiency.

Figure 2:
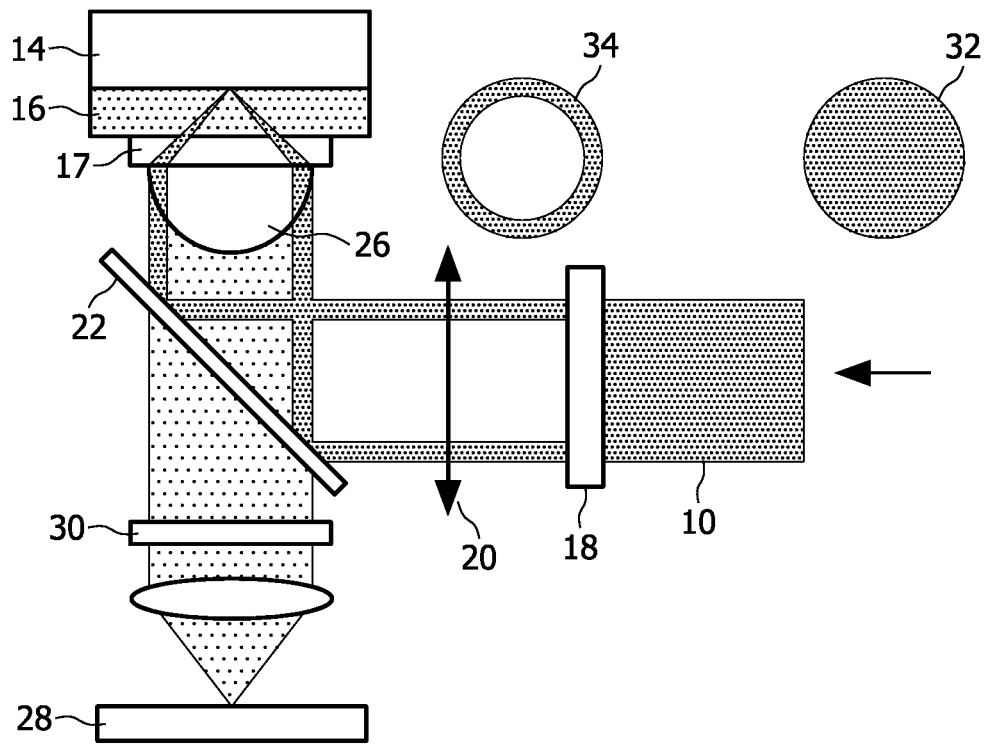
FIG. 2 shows an analysis apparatus of the invention.

FIG. 2 shows the basic components of a fluorescence scanner of an example of the invention. The sample 14 to be investigated is confined into a given volume forming a microfluidic part by a substrate 16. The lens includes an immersion fluid 17 as explained below. The excitation light 10 generated by a source such as a laser is used to excite fluorescence. The light is processed by an optical arrangement, which in this example comprises a beam transforming element 18 and a line forming element 20 (cylindrical lens or phase plate).

The processed excitation light is directed to the sample by a dichroic mirror 22, although a beam splitter can be used.

The excitation light is subsequently focused in the sample by means of an excitation lens 26, which can move relative to the sample.

The induced fluorescence, (as a result of the evanescent excitation light provided into the sample) is collected by a collection lens, which in this example is the same component as the excitation lens 26, and is directed toward a detector 28.

Any reflected laser light (the totally internally reflected light) is reflected again by the dichroic mirror or beam splitter 22, whereas the fluorescence luminance is passed through the mirror/beam splitter.

A band pass filter 30 provides further filtering for rejection of the excitation light, and the filtered light is focused on the detector 28 by an imaging lens 32 which images the sample onto the detector 28. Many different types of detector can be used, for example a photon tube multiplier and avalanche photodiode detector. A pixelated detector can be used.

FIG. 2 shows the intensity profile of the excitation light before (32) and after (34) passing through the beam shaping element 18. The intensity profile of the excitation light is transformed from a circular plane parallel wave front, to an annular cross section. The dimensions of the light annulus are matched with the physical dimensions of the lens 26, such that the light becomes evanescent in the bio-sample medium 14 after passing through the lens 26.

The light is focused by the complete optical system onto the substrate/bio-sample surface.

The line forming element 20 (cylindrical lens/phase plate) changes the light focus from a small spot, by disturbing the propagation of the wave front in one direction (for example the active direction of the cylindrical lens). The original spot in the focal plane of the lens 26 then becomes a line. The line is diffraction limited in one direction and its length is given by the divergence/convergence generated by the cylindrical lens/phase plate 20.

For the example of a cylindrical lens, the annular ring is transformed into a line at a distance equal to the focal length of the cylindrical lens. Between the lens and the focal distance, the shape of the optical cross section is a continuous transition from an annular ring to a line, through an elliptical ring. The cylindrical lens has a focal length that is much longer than the distance from the cylindrical lens 20 to the focusing lens 26. Therefore the shape of the beam when entering the focusing lens is a slightly elliptical annular ring.

Taking as parameter the desired line width (as produced by the focusing lens) the strength (focal length) of the cylindrical lens can be calculated, and implicitly the angular deviation introduced by it. This deviation is for example only of the order of few degrees.

Thus, the cylindrical lens functions as a line forming element, but the optical signal is processed further (by the focusing lens) before the line is formed. The output of the focusing lens is a line focused at the sample surface.

The use of a line enables scanning in only one direction in order to cover a two dimensional area of the sample. The line can for example have a length of around 100 microns, and a diffraction limited width of around 0.7 microns. The detection time can be reduced and/or the scanning speed can be reduced. A reduction in scanning speed is desirable particularly when the sample is moved, as the associated acceleration can interfere with the micro-fluidic properties of the sample.

In the embodiment shown in FIG. 2, the cylindrical lens/phase plate 20 is placed between the dichroic mirror 22 and the optical element 18 transforming the excitation beam. In practice, the cylindrical lens/phase plate can instead be placed between the dichroic mirror 22 and the lens 26 or before the optical element 18. The beam transformer 18 may also be placed at varying locations. However, it is preferably placed upstream of the dichroic beam splitter, because in that case the generated fluorescence can be collected without it being affected by the beam transformer.

The optical field of the excitation line is evanescent in the bio-sample medium, while tightly focused on the substrate/bio-sample surface. As a result it excites selectively only the fluorophores on the substrate/bio-sample surface.

The reflected excitation light (from the substrate/bio-sample surface) can be used for focus and/or tracking feedback loops. This secondary optical path is not shown in FIG. 2, and will not be described in detail, as conventional active focus and tracking arrangements for the excitation/collection lens 26 can be used in combination with the use of evanescent line excitation of the invention in combination with active focus/tracking.

The strength of the cylindrical lens 20, or the wave front distortions generated by a phase plate, are preferably limited such that the lateral extension of the line is within the field of the lens, i.e. the wave front distortions are kept below a desired value.

In order to create the evanescent excitation field, an immersion lens is preferably used. A solid immersion type lens can be used, also known as a "near field", or a liquid immersion type.

The condition to obtain an evanescent field at the substrate/bio-sample interface is given by:

$$\sin\alpha_{substrate} > \frac{n_{bio-sample}}{n_{substrate}},$$

with the condition that the lens refractive index (as well as the refractive index of the immersion fluid in the case of liquid immersion), is higher or equal that the refractive index of the substrate. From the same condition, it becomes obvious that the Numerical Aperture (NA) of the lens 26 has to fulfill:

$$NA_{imm.lens} > n_{bio-sample}$$

Figure 3:
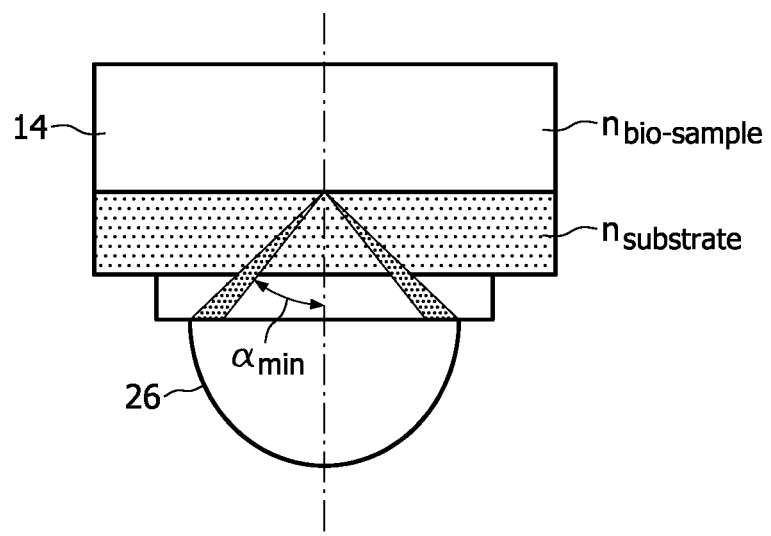
FIG. 3 shows how the light is shaped for generating an evanescent field.

Taking into account the lens geometry, the minimum angle condition ($\alpha_{min}$) translates into a minimum inner radius of the annular ring of light impinging on the immersion lens. This is illustrated in FIG. 3.

For fluorescence collection the full NA of the immersion lens is used.

Figure 4:
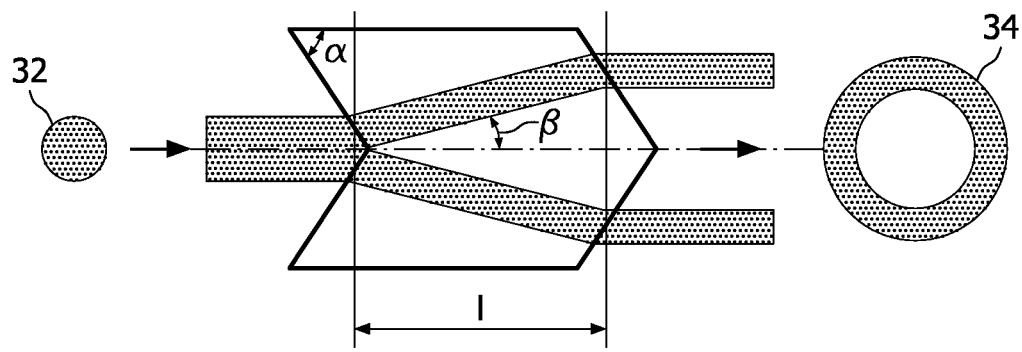
FIG. 4 shows a first example of beam shaping arrangement for use in the system of FIG. 2.

FIG. 4 shows in more detail one way of transforming a circular beam profile 32 into an annular beam 34. The optical element is has circular symmetry about the axis 40, and provides a beam splitting function by using angled incident faces. The element has conical input and output surfaces, which are used to diverge and then converge the light beam with respect to the axis 40. The input surface projects into the body of the element and the output surface projects out from the body of the element. This arrangement provides efficient light transformation as all the excitation light is used, potentially generating a more intense evanescent field. The parameters of the resulting annulus are determined by the characteristic angles of the optical element, α and β, as well as its length and the radius of the input beam.

Figure 5:
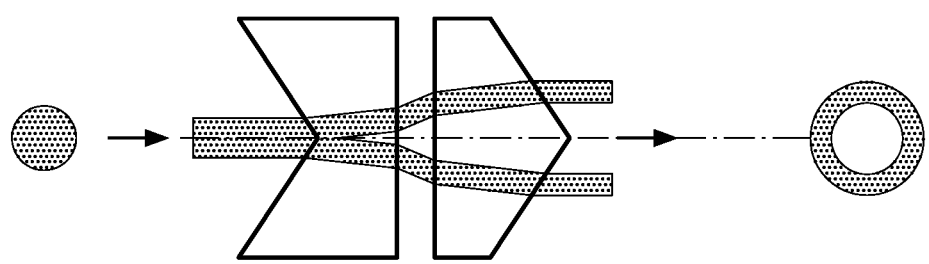
FIG. 5 shows a second example of beam shaping arrangement for use in the system of FIG. 2.
Figure 5:
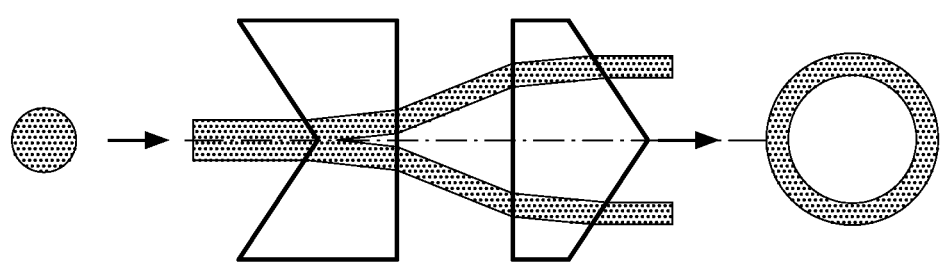

FIG. 5 shows a variation of the optical element of FIG. 4. The optical element is split into two components. The input component has a conical input surface (projecting into the body of the element) and a planar output surface, and the output component has a planar input surface and a conical output surface (projecting out of the body of the element).

The dimensions of the resulting annulus can be adjusted by modifying the distance between the two parts, as shown in FIG. 5.

The present invention is not limited to the method described above for obtaining an annulus of light. Other methods, for example a phase-plate, an annular diaphragm or dichroic rings can be used as well. As an alternative, a Schwarzshield objective can also be used, where the incident light is reflected towards parabolic mirrors which results in a focused annular spot behind the objective.

In the examples above, the system is used for fluorescence detection. However, the invention more generally relates more generally to the excitation of a sample and the detection of resulting light. The induced luminescence can for example comprise phosphorescence.

In the examples above, a dichroic beam splitter DBS is used, as the preferred solution. However a normal (non-dichroic) beam splitter can be used as well, although some excitation power as well as collected fluorescence would be wasted.

The substrate may be a flat plate of any suitable material, e.g. may be of glass or a polymer, and may have capture elements with a surface density between 0.01 and $10^6$ elements per $\mu m^2$, preferably between 10 and $10^4$ elements per $\mu m^2$.

The sample, the substrate with capture elements in contact with the sample or the substrate after it has been in contact with the sample, typically is screened for certain components, e.g. biological components such as oligonucleotides, DNA, RNA, genes, proteins, carbohydrates, lipids, cells, cell components such as external cell membranes or internal cell membranes, bacteria, viruses, protozoa, etc. also called the target particles.

Luminescent labels typically are attached to the target particles and thus assist in the detection of target particles. In some embodiments the sample thus includes at least one luminescent label, also referred to as an "optically variable particle". Such optically variable particles can be, for instance, fluorescent (as described above), electroluminescent or chemiluminescent particles. The optical variable particles may be any entity that is capable to bind to a binding site mechanically, electrically, chemically or otherwise. It may comprise single molecules or a plurality of molecules, preferably a collection of between 10 to $10^8$ molecules and/or quantum dot-like labels. If a plurality of molecules is used, typically a stronger response to the excitation is obtained, resulting in a better signal-to-noise ratio.

The applications of the invention are generally in the field of molecular diagnostics: clinical diagnostics, point-of-care diagnostics, advanced bio-molecular diagnostic research—biosensors, gene and protein expression arrays, environmental sensors, food quality sensors, etc.

Various other modifications will be apparent to those skilled in the art. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. In the device claim enumerating several means, several of these means may be embodied by one and the same item of hardware. The mere fact that certain measures are recited in mutually different dependent claims does not indicate that the combination of these measures cannot be used to advantage.

The invention claimed is:

1. An illumination detection system, comprising:
   an excitation radiation source and associated radiation processing arrangement for providing excitation radiation;
   a focusing arrangement for focusing the excitation radiation onto an analysis region of a sample;
   a radiation collection arrangement for collecting analysis radiation from the analysis region of the sample and resulting from the excitation; and
   a detector for detecting the collected analysis radiation, wherein the focused excitation radiation comprises an excitation line which is evanescent in the sample,
   wherein the radiation processing arrangement comprises a beam shaping element for generating an annular beam shape, and
   wherein the radiation processing arrangement comprises a line forming element for generating a beam shape from the annular beam which is mapped by the focusing arrangement to the excitation line.

2. The illumination detection system as claimed in claim 1, wherein the beam shaping element generates the annular beam shape from a plane parallel circular cross section wave front at the output of the excitation radiation source.

3. The illumination detection system as claimed in claim 1, wherein the line forming element has a focal distance longer than the distance between the line forming element and the focusing arrangement.

4. The illumination detection system as claimed in claim 1, wherein the line forming element comprises a cylindrical lens or phase plate.

5. The illumination detection system as claimed in claim 1, wherein the radiation collection arrangement is for collecting analysis radiation in a form of luminescence radiation.

6. The illumination detection system as claimed in claim 1, comprising a biological component screening system.

7. The illumination detection system as claimed in claim 1, wherein the focusing arrangement and the radiation collection arrangement share an excitation/collection lens.

8. The illumination detection system as claimed in claim 1, wherein the detector comprises a pixilated light detector.

9. A method of measuring an analysis radiation from a sample using an illumination detection system, comprising:
   generating excitation radiation;
   processing the excitation radiation;
   focusing the processed excitation radiation such than an excitation line which is evanescent in the sample is provided at an analysis region of a sample;
   collecting the analysis radiation resulting from the excitation from the analysis region; and
   detecting the collected analysis radiation,
   wherein the excitation radiation processing comprises using a line forming element to generate a beam shape from the annular beam which is mapped by the focusing arrangement to an excitation line.

10. The method as claimed in claim 9, wherein collecting the analysis radiation comprises collecting luminescence radiation from the sample.

11. The method as claimed in claim 9 comprising a biological component screening method.

12. The method as claimed in claim 9, wherein the excitation radiation processing comprises generating an annular beam shape from a plane parallel circular cross section wave front at an output of the excitation radiation source.

* * * * *